United States Patent
Pennington et al.

(10) Patent No.: US 6,723,078 B1
(45) Date of Patent: Apr. 20, 2004

(54) EMERGENCY URINAL KIT

(76) Inventors: Vinroy Pennington, P.O. Box 1126, Wurtsboro, NY (US) 12790; Aston Pennington, P.O. Box 1126, Wurtsboro, NY (US) 12790

(*) Notice: Subject to any disclaimer, the term of this patent is extended or adjusted under 35 U.S.C. 154(b) by 99 days.

(21) Appl. No.: 10/191,826

(22) Filed: Jul. 9, 2002

Related U.S. Application Data

(63) Continuation of application No. 09/686,217, filed on Oct. 11, 2000.

(51) Int. Cl.$^7$ .................................................. A61M 1/00
(52) U.S. Cl. ....................................................... 604/327
(58) Field of Search ................................ 604/317, 319, 604/322, 323, 326, 327, 331, 346, 347, 349, 350

(56) References Cited

U.S. PATENT DOCUMENTS

| | | | | |
|---|---|---|---|---|
| 3,897,785 A | * | 8/1975 | Barto, Jr. ...................... | 604/327 |
| 4,173,979 A | * | 11/1979 | Odis .............................. | 604/327 |
| 4,387,726 A | * | 6/1983 | Denard ......................... | 600/573 |
| 4,421,509 A | * | 12/1983 | Schneider et al. ............ | 604/317 |
| 4,511,358 A | * | 4/1985 | Johnson et al. .............. | 604/327 |
| 4,813,943 A | * | 3/1989 | Smith ........................... | 604/329 |
| 5,263,946 A | * | 11/1993 | Klug ............................. | 604/327 |
| 5,354,132 A | * | 10/1994 | Young et al. ................. | 383/49 |
| 5,411,495 A | * | 5/1995 | Willingham .................. | 604/329 |
| 5,423,792 A | * | 6/1995 | Oxley ........................... | 604/409 |
| 5,454,797 A | * | 10/1995 | Haswell ........................ | 604/317 |
| 5,496,300 A | * | 3/1996 | Hirsch et al. ................. | 604/327 |
| 5,531,724 A | * | 7/1996 | Young et al. ................. | 604/327 |
| 5,571,095 A | * | 11/1996 | Lu ................................ | 604/329 |
| 5,645,541 A | * | 7/1997 | Bouser ......................... | 604/353 |
| 5,735,837 A | * | 4/1998 | Ishikawa ................ | 604/385.09 |
| 5,865,821 A | * | 2/1999 | Lowey .......................... | 604/352 |
| 5,894,608 A | * | 4/1999 | Birbara ......................... | 34/144.3 |
| 5,935,116 A | * | 8/1999 | Kristensen ................... | 604/353 |
| 5,961,501 A | * | 10/1999 | Cassidy et al. .............. | 604/327 |
| 6,039,060 A | * | 3/2000 | Rower ......................... | 134/167 R |
| 6,183,454 B1 | * | 2/2001 | Levine et al. ................ | 604/329 |
| 6,296,627 B1 | * | 10/2001 | Edwards ....................... | 604/347 |

FOREIGN PATENT DOCUMENTS

GB      2 215 211 A    *   9/1989            A61F/5/44

\* cited by examiner

*Primary Examiner*—John J. Calvert
*Assistant Examiner*—Michael Bogart
(74) *Attorney, Agent, or Firm*—John D. Gugliotta; Olen L. York, III

(57) ABSTRACT

An emergency urinal kit is provided having a urine receptacle and a pair of specifically adapted male and female collector funnels, each said collector funnel for interchangeable connection with said urine receptacle for provide fluid communication thereto. The male collector funnel forms a cylindrical flexible membrane that has a rollable sidewall and is in fluid communication with a drain tube for connection with a collection conduit. The female collector funnel forms a rigid sidewall terminating at the upper end in an upper sealing ridge forming a contoured upper edge specifically adapted to seal against the user's body when pressed against the user's groin, and is in fluid communication with a drain tube for connection with a collection conduit.

14 Claims, 3 Drawing Sheets

EMERGENCY URINAL KIT

RELATED APPLICATIONS

The present invention is a continuation of U.S. patent application Ser. No. 09/686,217 filed Oct. 11, 2000.

BACKGROUND OF THE INVENTION

1. Field of the Invention

The present invention relates generally to urine receptacles and the like and, more particularly, to a urine collection device having a pair of male and female collector funnels in combination with a standard water hose connection for flushing and detachable inlet hoses capable of being carried in a pocket formed at the side of the device.

2. Description of the Related Art

Embarrassment is perhaps the worst aspect for people suffering from incontinence. Not only do accidents themselves cause embarrassment, the solution of incontinence pads or "adult diapers" leads to embarrassment as well. These pads are often bulky and can be clearly seen in outline form under one's clothes. Additionally, they are uncomfortable and hot to wear especially in warm weather. People who do not suffer from incontinence, but a weak bladder or frequent urination also suffer from similar problems. It is sometimes almost impossible to sleep or travel in a car due to the need to urinate frequently.

A search of the prior art did not disclose any patents that read directly on the claims of the instant invention; however, the following references were considered related.

The following patents disclose a garment for fixing a urine bag on a user.

U.S. Pat. No. 5,935,116 issued in the name of Kristensen

U.S. Pat. No. 4,421,509 issued in the name of Schneider et al.

U.S. Pat. No. 4,173,979 issued in the name of Odis

The following patents describe a support system for a catheter leg bag.

U.S. Pat. No. 5,865,821 issued in the name of Lowey

U.S. Pat. No. 3,897,785 issued in the name of Barto, Jr.

U.S. Pat. No. 5,735,837 issued in the name of Ishikawa discloses a urine absorbent bag for male incontinence.

U.S. Pat. No. 5,571,095 issued in the name of Lu describes a disposable urine bag for females.

U.S. Pat. No. 4,511,358 issued in the name of Johnson, Jr. et al. discloses a urine bag carrier with a stretchable front panel.

And, U.S. Pat. No. 4,387,726 issued in the name of Denard describes a disposable urine collection device for males.

Consequently, there exists a need for a means by which those who suffer from incontinence, a weak bladder or frequent urination can be afforded a solution to this problem in a manner which is inconspicious to all of those around.

SUMMARY OF THE INVENTION

Therefore, it is an object of the invention to provide for an improved urine receptacle for males and females.

It is a feature of the present invention to provide a urine collection device specifically adapted to conform in shape to the frontal contours of the wearer's body.

It is another feature of the present invention to provide a urine collection device having a valved drain mechanism.

Briefly described according to one embodiment of the present invention, an emergency urinal kit is a urine collection system for people suffering from incontinence, people who are bedridden, or people who do not have easy access to restroom facilities, such as those who are traveling. The invention consists of a pair of small rubber collection funnels, attached to a corresponding connection hose and a corresponding inlet valve. The person simply places the collection funnel against the urination opening and relieves themselves. The rubber tube carries the urine to a flexible, soft plastic collection bag, where escaping air exits through an air relief valve. When finished, the user simply closes all valves. To empty the device, the user opens the air relief valve and an exit valve on the bottom. The device is then washed out and rinsed and stored in a carrying case for the next time it is needed. A carrying strap provides for easy transportation.

The use of the present invention allows or those unable to use a restroom or bathroom the ability to relieve themselves in a discrete manner that is quick, easy and effective.

An advantage of the present invention is that it provides for a pair of male and female urine receptacles having a valved drain mechanism.

BRIEF DESCRIPTION OF THE DRAWINGS

The advantages and features of the present invention will become better understood with reference to the following more detailed description and claims taken in conjunction with the accompanying drawings, in which like elements are identified with like symbols, and in which:

DESCRIPTION OF THE PREFERRED EMBODIMENTS

1. Detailed Description of the Figures

Figure 1:
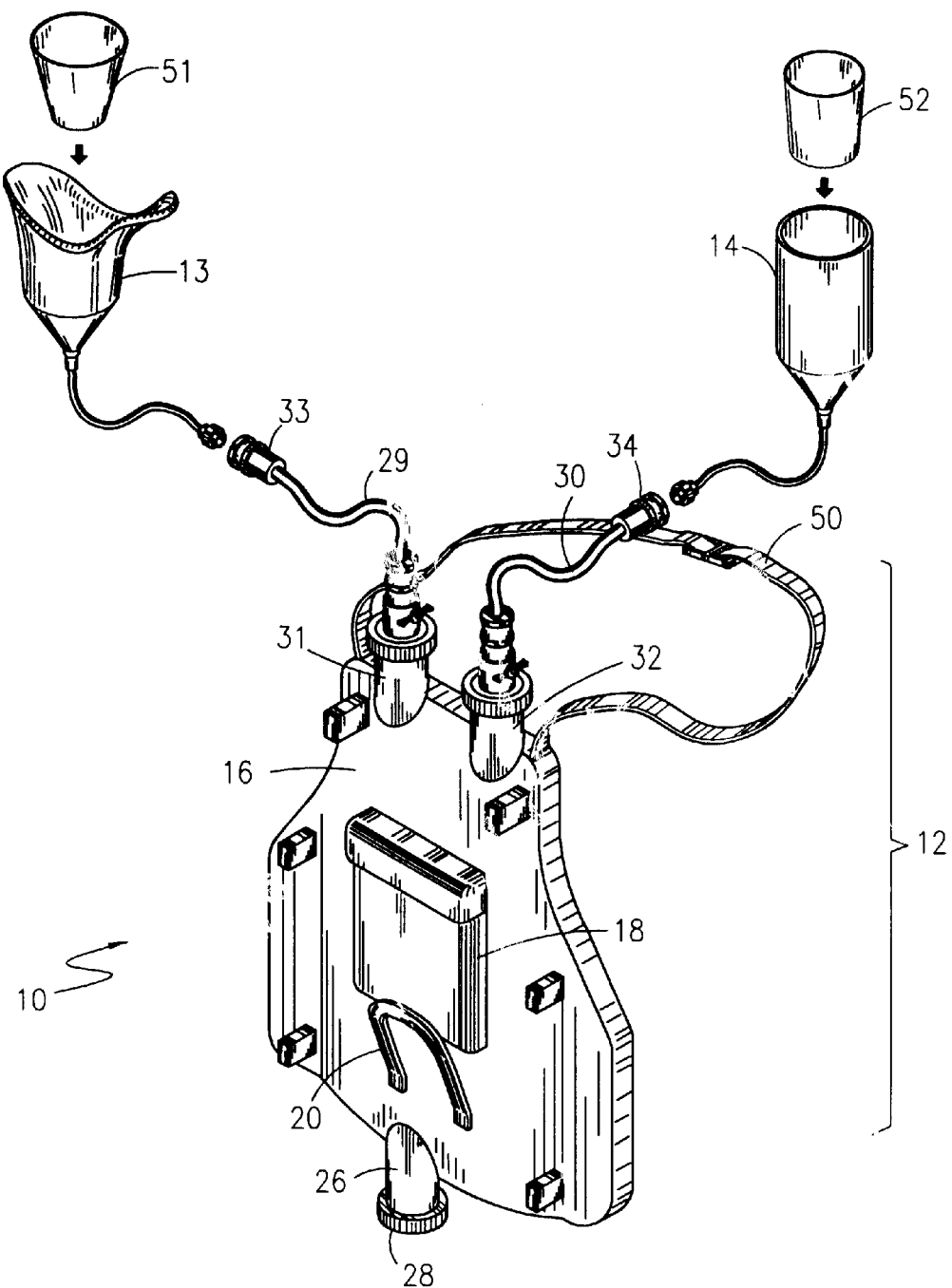
FIG. 1 is a perspective view of an emergency urine kit according to the preferred embodiment of the present invention.
Figure 2:
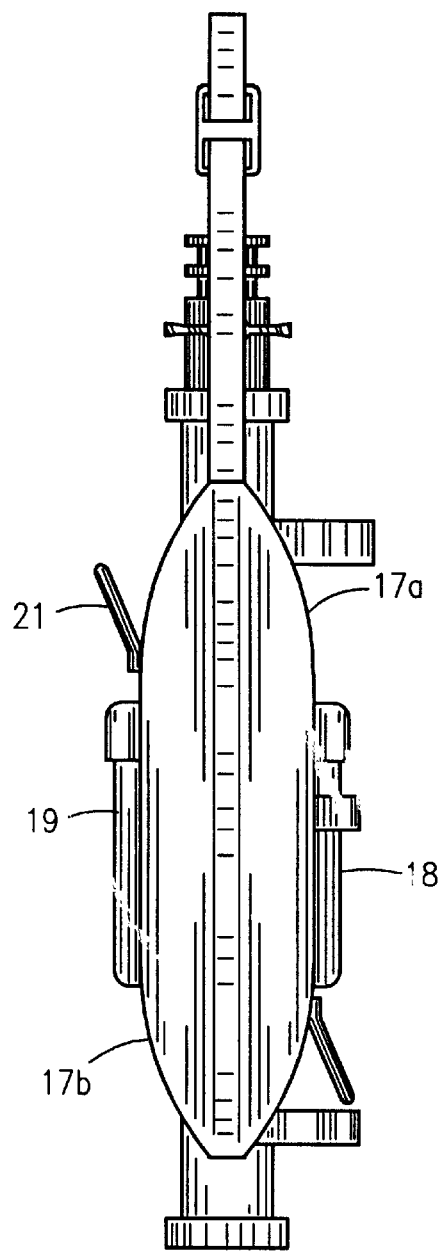
FIG. 2 is a side elevational view thereof.

Referring now to FIGS. 1–2, an emergency urinal kit, generally noted as 10, is provided including a urine receptacle 12 in conjunction with a pair of collector funnels, specifically adapted as a female collector funnel 13 and male collector funnel 14. The female collector funnel 13 has a corresponding female plug 51, and the male collector funnel 14 has a corresponding male plug 52, each designed to fit securely within the respective collector funnel openings and for providing added security against urine backing into the and through the respective conduits 29 or 30 and out the collector funnels 13 or 14. According to the present invention, the urine receptacle 12 is formed of a centrally disposed collection receiver 16 having a front receiver surface 17a parallel to and opposite a rear receiver surface 17b. Each receiver surface 17a, 17b is anticipated as being a generally pliable vertical sidewall supporting a pocket 18 which forms an internal volume (not shown) and having an entry orifice releasably closed by a pocket flap 19. Along the lower portion of the front receiver surface is a lower support hook 20. Formed as a linear fabric strap or elastic cord, the lower support hook 20 is affixed at each end to the front receiver surface and forms a grasping loop allowing the user to support the urine receptacle 12 upon an available hook or similar environmental supportive structure. Along the upper portion of the rear receiver surface 17b is an upper support hook 21. Similarly formed as a linear fabric strap or elastic cord, the upper support hook 21 is affixed at each end to the rear receiver surface 17b and forms a grasping loop allowing the user to support the urine receptacle 12 upon an available hook or similar environmental supportive structure.

Along the lowermost seam of the collection receiver 16 is a receiver discharge 26 in fluid communication with the internal volume of the collection receiver 16. Terminating the receiver discharge 26 is a discharge valve 28 for controllably releasing the contents of the collection receiver 16. Along the uppermost seam of the collection receiver 16 is a pair of collection conduits 29 and 30 and a pair of receiver flushing ports 31 and 32. The collection conduits 29 and 30 are in fluid communication with the internal volume of the collection receiver 16, and each has a releasable connection 33 or 34 for connection with any of the series of specifically adapted collector funnels 13 or 14. The collection conduits 29 or 30 are envisioned as a linearly elongated plastic tube or hose for allowing easy, general manipulation of the collector funnels 13 or 14 and allows for collection and transmission of urine to the collection receiver 16.

Figure 3:
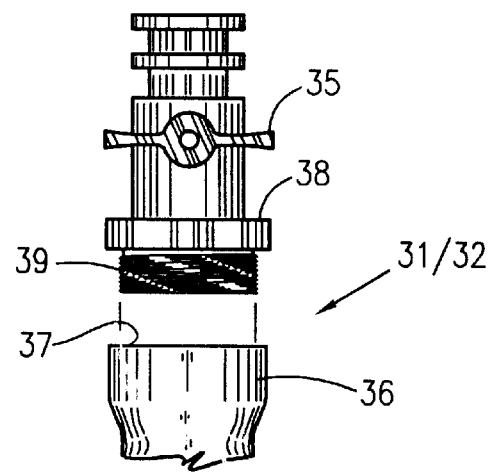
FIG. 3 is a detailed partial elevational view of a receiver flushing port 32 for use with the present invention.

In conjunction with FIG. 3, a receiver flushing port 31 or 32 is shown in greater detail. A receiver nozzle 36 forms a means of fluid communication with the internal volume of the collection receiver 16. The receiver nozzle 36 forms an internal female thread 37 for threadably engaging with a conventionally available garden hose. In this manner, the interior volume of the collection receiver 16 can be thoroughly flushed and rinsed adequately and easily with water after, before, or between uses. A sealing cap 38 forms a plug having male threads 39 for threadably engaging with the internal female threads 37 to seal the collection receiver 16 during use. A valve 35 is provided along the receiver flushing port 31 or 32 for opening and closing the junction between the conduit 29 or 30 and the flushing port 31 or 32, thus preventing urine from backing up from the collection receiver 16 into the conduit 29 or 30.

Further, a support attachment 50 is designed as a hanger/carrier for hand carrying or to hang about a user's neck.

Figure 4A:
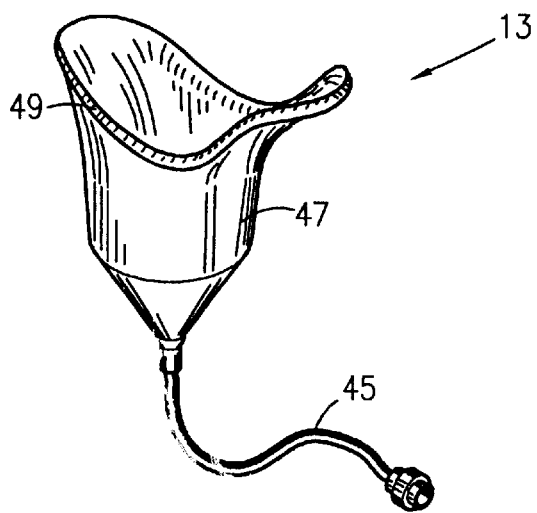
FIG. 4a is a female collector funnel 13 for use with the present invention.
Figure 4B:
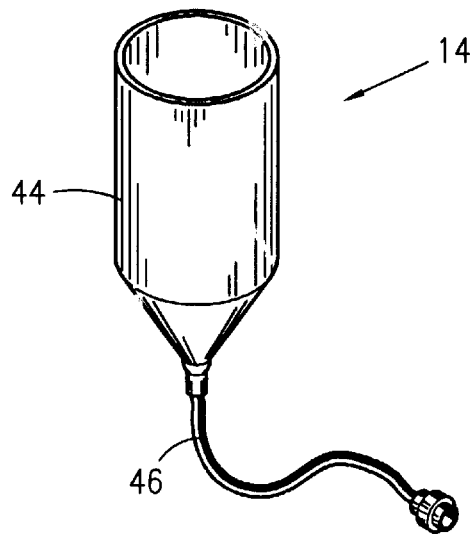
FIG. 4b is a male collector funnel 14 for use with the present invention.
Figure 4C:
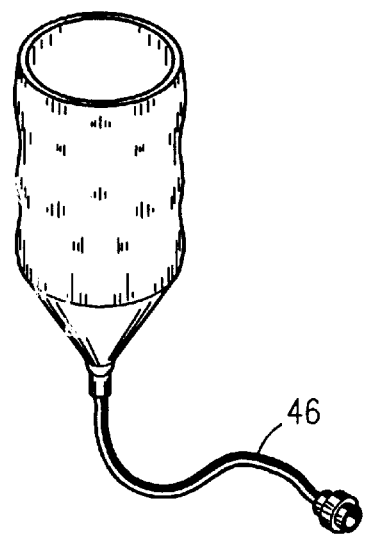
FIG. 4c is an alternate embodiment for a male collector funnel for use with the present invention.

Finally, in FIG. 4a, FIG. 4b, the female collector funnel 13 and the male collector funnel 14 are shown. It is envisioned that the collector funnels 13 and 14 would be formed such as to be easily and inexpensively disposable. A female collector funnel 13 forms a rigid sidewall 47 terminating at the upper end in an upper sealing ridge 49. The upper sealing ridge 49 forms a contoured upper edge specifically adapted to seal against the user's body when pressed against the user's groin, forming an easy collection point for communication of urine to a drain tube 45 for connection with the collection conduit 29. The male collector funnel 14 forms a cylindrical sidewall. In an alternate embodiment, as shown in FIG. 4c, the sidewall is formed of a flexible membrane 44 that is rollable. In this manner, the sidewall can be stored in a compact, rolled condition and deployed by "unrolling" the flexible sidewall. This is especially useful for bedridden or infirm individuals. In either case, the interior volume of the male collector funnel 40 is in fluid communication with a drain tube 46 for connection with the collection conduit 30.

2. Operation of the Preferred Embodiment

The use of the present invention allows men or women suffering form mild cases of incontinence the ability to lead a normal lifestyle in a manner that is quick, easy and effective. The invention provides a means for those men and women who cannot quite make to a restroom before urination begins. To use, a male or female will remove the appropriate and corresponding plug 51 or 52 and position the male or female collector funnel 13 or 14 against his or her groin. The user will turn the corresponding valve 35 to open the junction between the conduit 29 or 30 and the receiver flushing port 31 or 32. The user will then relieve themselves into the collector funnel 13 or 14, with the urine traveling through the drain tube 45 or 46, the collection conduit 29 or 30, the receiver flushing port 31 or 32, and into the collection receiver 16 for storage until disposed of. After use, the collection receiver 16 can be completely drained or urine and then thoroughly rinsed with disinfectant, soap and/or water.

As designed, a device embodying the teachings of the present invention is easily applied. The foregoing description is included to illustrate the operation of the preferred embodiment and is not meant to limit the scope of the invention. As one can envision, an individual skilled in the relevant art, in conjunction with the present teachings, would be capable of incorporating many minor modifications that are anticipated within this disclosure. Therefore, the scope of the invention is to be broadly limited only by the following claims.

What is claimed is:

1. An emergency urinal kit comprising:

a urine receptacle;

a pair of specifically adapted collector funnels, wherein said pair of collector funnels include a female collector funnel, adapted for use by a female, and a male collector funnel, adapted for use by a male, wherein said collector funnels further provide fluid communication with said receptacle;

a discharge orifice affixed along a lowermost seam of a collection receiver, said discharge orifice in fluid communication with the internal volume of said collection receiver; and a discharge valve terminating said discharge orifice for controllably releasing the contents of said collection receiver.

2. The emergency urinal kit of claim 1 farther comprising a pair of specifically adapted plugs, wherein said pair of plugs include a female plug, adapted for secure insertion into female collector funnel, and a male plug, adapted for secure insertion into male collector funnel, wherein said plugs provide a means for preventing collected urine from backing out of said emergency urinal kit.

3. The emergency urinal kit of claim 1, further comprising a support attachment affixed to said urine receptacle.

4. The emergency urinal kit of claim 1, wherein said male collector funnel forms a cylindrical flexible membrane that has a rollable sidewall and is in fluid communication with a drain tube for connection with a collection conduit.

5. The emergency urinal kit of claim 1, wherein said female collector funnel forms a rigid sidewall terminating at the upper end in an upper sealing ridge forming a contoured upper edge specifically adapted to seal against the user's body when pressed against the user's groin, said female collector funnel in fluid communication with a drain tube for connection with a collection conduit.

6. An emergency urinal kit comprising:

a urine receptacle formed of a centrally disposed collection receiver having a front receiver surface parallel to and opposite a rear receiver surface, each said receiver surface supporting a pocket forming an internal volume and having an entry orifice releasably closed by a pocket flap; and a pair of specifically adapted collector funnels, wherein said pair of collector funnels include a female collector funnel, adapted for use by a female, and a male collector funnel, adapted for use by a male, wherein said collector funnels further provide fluid communication with said receptacle.

7. The emergency urinal kit of claim 6 further comprising:

a lower support hook affixed along the lower portion of the front receiver surface, said lower support hook forming a linear fabric strap affixed at each end to the front receiver surface and forms a grasping loop allowing the user to support the urine receptacle; and a upper support hook affixed along the upper portion of the rear receiver surface, said lower support hook forming a linear fabric strap affixed at each end to the rear receiver surface and forms a grasping loop allowing the user to support the urine receptacle.

8. The emergency urinal kit of claim 6, further comprising a support attachment affixed to said urine receptacle.

9. The emergency urinal kit of claim 6, wherein said male collector funnel forms a cylindrical flexible membrane that has a rollable sidewall and is in fluid communication with a drain tube for connection with a collection conduit.

10. The emergency urinal kit of claim 6, wherein said female collector funnel forms a rigid sidewall terminating at the upper end in an upper sealing ridge forming a contoured upper edge specifically adapted to seal against the user's body when pressed against the user's groin, said female collector funnel in fluid communication with a drain tube for connection with a collection conduit.

11. An emergency urinal kit comprising:

a urine receptacle;

a pair of specifically adapted collector funnels, wherein said pair of collector funnels include a female collector funnel, adapted for use by a female, and a male collector funnel, adapted for use by a male, wherein said collector funnels further provide fluid communication with said receptacle;

a collection conduit along an uppermost seam of the collection receiver, said collection conduit in fluid communication with an internal volume of said collection receiver and has a releasable connection for connection with any of said collector funnels;

a pair of receiver flushing ports, wherein each said receiver flushing port is formed of a receiver nozzle forming a means of fluid communication with said internal volume of said collection receiver, and having an internal female thread for threadably engaging with a conventionally available garden hose; and a pair of sealing caps, wherein each said sealing cap forms a plug having male threads for threadably engaging with the internal female threads to seal said respective collection receiver.

12. The emergency urinal kit of claim 11, further comprising a support attachment affixed to said urine receptacle.

13. The emergency urinal kit of claim 11, wherein said male collector funnel forms a cylindrical flexible membrane that has a rollable sidewall and is in fluid communication with a drain tube for connection with a collection conduit.

14. The emergency urinal kit of claim 11, wherein said female collector funnel forms a rigid sidewall terminating at the upper end in an upper sealing ridge forming a contoured upper edge specifically adapted to seal against the user's body when pressed against the user's groin, said female collector funnel in fluid communication with a drain tube for connection with a collection conduit.

\* \* \* \* \*